United States Patent [19]

Beer

[11] Patent Number: 4,912,735
[45] Date of Patent: Mar. 27, 1990

[54] POWER TRANSFER APPARATUS PARTICULARLY FOR CT SCANNER

[75] Inventor: Steve Beer, Burlington, Mass.

[73] Assignee: Elscint Ltd., Haifa, Israel

[21] Appl. No.: 220,680

[22] Filed: Jul. 18, 1988

[51] Int. Cl.$^4$ .............................................. H05G 1/60
[52] U.S. Cl. ............................................ 378/15; 378/4
[58] Field of Search ...................................... 378/15, 4

[56] References Cited

U.S. PATENT DOCUMENTS

| | | | |
|---|---|---|---|
| 4,223,313 | 9/1980 | Chabrol | 336/83 |
| 4,321,572 | 3/1982 | Studer et al. | 340/207 |
| 4,323,781 | 4/1982 | Baumann et al. | 378/15 |
| 4,723,259 | 2/1988 | Amor et al. | 378/15 |
| 4,796,183 | 1/1989 | Ermert et al. | 378/15 |

Primary Examiner—Craig E. Church
Attorney, Agent, or Firm—Sandler & Greenblum

[57] ABSTRACT

A CT scanner comprises a static gantry member and a rotatable member mounted on the gantry member for rotation about a central axis. A stationary power supply is associated with the gantry member for supplying power to an x-ray tube mounted on the rotatable member. An inductive coupling is responsive to the power supply for transmitting electrical power to the x-ray tube from the gantry member. The x-ray tube is operable in response to the transmitted power for producing x-ray beams passing through the central axis.

23 Claims, 2 Drawing Sheets

POWER TRANSFER APPARATUS PARTICULARLY FOR CT SCANNER

DESCRIPTION

1. Technical Field

This invention relates to power transfer apparatus, particularly for a CT scanner, for efficiently and reliably transferring power between a stationary member and a rotatable member.

2. Background Art

Most computerized tomograhic (CT) scanners in present use are designed to operate as either "rotate-rotate" (or "third generation") scanners, or "rotate-only" (or "fourth generation") scanners. A "rotate-rotate" scanner is one in which both the x-ray tube and the detector array are mounted on a common member that is rotatable on a stationary member about a central axis. A "rotate-only" scanner is one in which only the x-ray tube is rotatable on a stationary member about a central axis, the detectors being mounted on the stationary member so as to be coaxial and coplanar (at a larger radius than the tube radius) with the path followed by the x-ray tube. In both cases, the stationary member is provided with a central axial aperture concentric with the axis of rotation of the x-ray tube. The aperture has an axial length just greater than the height of a normal person, and a diameter of about 2 m. allowing a prone patient to be moved into and out of the scanner along its central axis. As a result of this configuration, most scanners mount the x-ray tube on a rotatable ring that is supported on bearings carried by a stationary ring.

To operate the x-ray tube, electrical power in the range of 20–60 KW must be transferred to the rotatable ring; and a final operating voltage in the range of 100–150 KV must be supplied to the tube. Conventionally, the required power is transmitted to the rotatable member carrying the x-ray tube via flexible high voltage (HV) cables. In such case, a cable uptake or spooling system must be provided sufficient to enable at least one complete rotation of the tube to take place.

Alternately, a "slip-ring" design can be used whereby power is transferred from the stationary member to the rotatable member via a sliding contact enabling infinite angular rotation. A slip-ring can be designed for operation at either low voltage (i.e., power line voltage), or high voltage (i.e., comparable to the operating voltage of the tube). If a low-voltage slip-ring is utilized, a voltage step-up stage must be included on the rotatable member to provide the required high voltage for operation of the x-ray tube.

Although the slip-ring approach for power transfer is usually preferred over the use of flexible high voltage cables, such approach has several drawbacks. Among the drawbacks are cost and complexity of manufacture due to the special materials and mechanical precision required because of the power levels involved, and the cost of operation because of the need for periodic maintenance and replacement of wearable components.

It is therefore an object of the present invention to provide a new and improved power transfer transfer apparatus, particularly for a CT scanner, which overcomes deficiencies associated with conventional slip-ring/brush configurations of the prior art.

BRIEF DESCRIPTION OF INVENTION

Power transfer apparatus according to the present invention comprises a static member and a rotatable member mounted on the static member for rotation about a central axis. Such apparatus also includes a ring of high permeability mounted on the static member, and a ring of high permeability mounted on the rotatable member. The axis of each ring is coincident with the central axis. Finally, inductive coupling means is associated with each ring for transferring electrical power between the static member and the rotatable member.

The rings have opposed annular faces, each of which contains at least one annular groove, the groove in one ring being aligned with the groove in the other ring; and the inductive coupling means includes a circumferential conductive winding located in each annular groove. Power supply means are provided for applying a high frequency alternating electrical current to one of the windings whereby an alternating electric current is induced in the other of the windings. Preferably, the opposed annular faces on the ring define closely spaced, axially disposed planes perpendicular to the central axis. Optionally, the opposed faces may be closely spaced concentric cylindrical surfaces.

Highly permeable rings of a size compatible with the requirements for a CT scanner are relatively inexpensive and easy to fabricate and provide part of an inductive power transfer apparatus which eliminates mechanical contact between the rings thereby improving both performance and maintenance characteristics of the scanner.

BRIEF DESCRIPTION OF THE DRAWINGS

Embodiments of the invention are disclosed in the accompanying drawings wherein.

DETAILED DESCRIPTION

Figure 1:
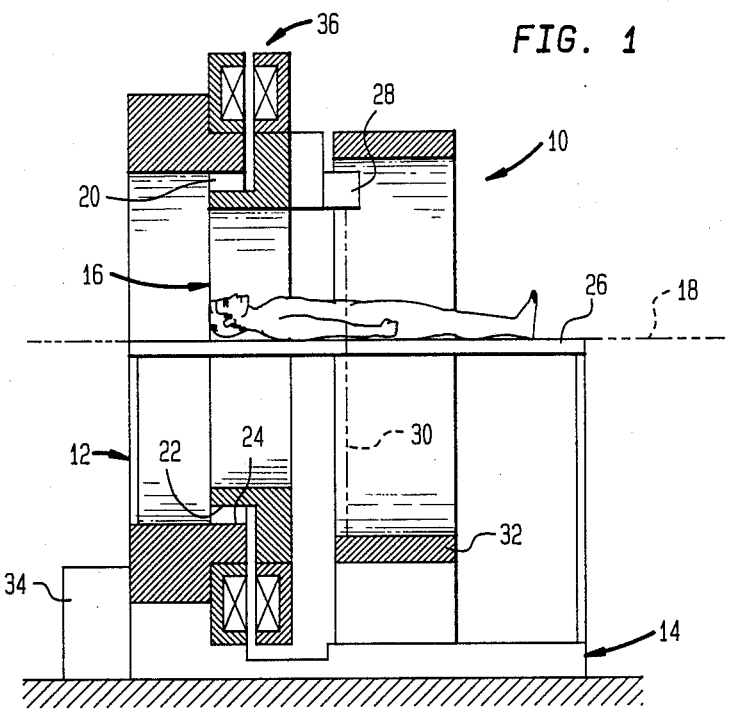
FIG. 1 is a schematic vertical section through a fourth generation CT scanner for the purpose of illustrating inductive power transfer apparatus according to the present invention.

Referring now to the drawings, reference numeral 10 designates a CT scanner according to the present invention. Scanner 10 comprises static gantry member 12 rigidly supported on base 14, and rotatable member 16 mounted on the gantry member for rotation about central axis 18. Suitable roller bearings schematically indicated by reference numeral 20 are circumferentially disposed on inner race 22 attached to the rotatable member and are engaged with outer race 24 on the stationary member. In this manner, rotatable member 16 is freely rotatable about axis 18. Physically, the diameter of member 16 is approximately 2 m., this configuration of the ring providing clearance for rigidly mounting patient support table 26 substantially along axis 18.

Rigidly attached to rotatable member 16 X-ray tube 28 which is designed, in a conventional manner, to produce a fan beam of radiation 30 whose apex is located at the X-ray tube, and which passes through axis 18. The fan beam is incident on a stationary cylindrical array of detectors 32, the axis of which is coincident with axis 18. Power supply 34 associated with stationary member 12 provides the power for operating X-ray tube 28.

In order to transmit electrical power from the power supply means to X-ray tube 28, inductive coupling means 36 according to the present invention is provided. Means 36 is thus responsive to power supply 34 for transmitting electrical power from the stationary member to the rotatable member. X-ray tube 28 mounted on the rotatable member is operable in response to power transmitted to the rotatable member for producing X-ray beams as indicated above.

Inductive coupling means 36 according to the present invention includes a highly permeable ring mounted on the stationary member, a highly permeable ring mounted on the rotatable member, at least one winding on the ring mounted on the stationary member, and at least one winding on the ring mounted on the rotatable member. Each of these windings has an axis coincident with central axis 18 and is in the form of an azimuthally wound conductor.

Figure 5A:
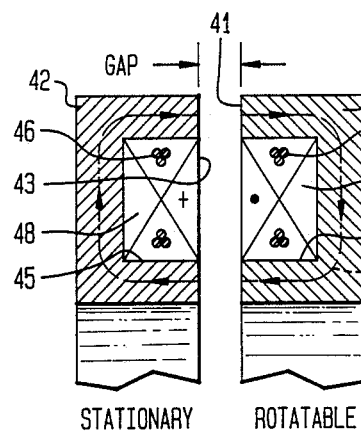
FIGS. 5a and 5b show two different embodiments of the present invention.

FIG. 5a illustrates one embodiment of inductive coupling means 36. As shown in FIG. 5a, rotatable ring 40, which is mounted on rotatable member 16, has annular face 41 facing annular face 43 of ring 42 mounted on stationary member 12. Faces 41 and 43 are axially displaced but are actually very close to each other so that a small air gap exists between the two faces. These rings are highly permeable material such as ferrite; and each of the annular faces contains at least one annular groove, the axis of which is concentric with axis 18. In the embodiment shown in FIG. 5a, face 41 is provided with groove 44, and face 43 is provided with groove 45 aligned with groove 44. Each of these grooves contains azimuthally wound conductors 46. The conductors wound in groove 44 define coil 47; and the conductors wound in groove 45 define winding 48.

Figure 5B:
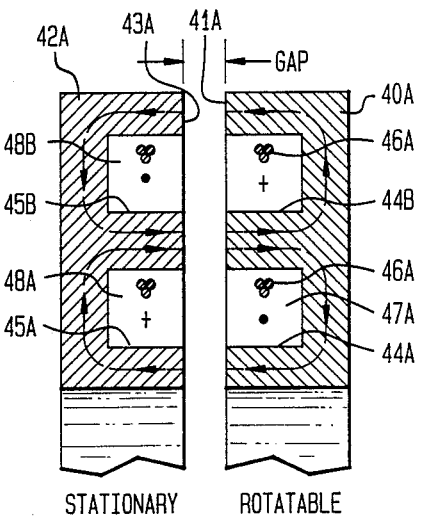

A power supply, such as power supply 34, applies a high frequency alternating current to winding 48 contained in groove 45 of stationary ring 42. When the instantaneous direction of current flow in winding 45 is as indicated in FIG. 5a (i.e., into the paper), the direction of the flux in ring 42 is as indicated by flux arrows 49 (i.e., clockwise) as shown in FIG. 5b. The relatively small axial gap between the opposing faces 41 and 43 does not significantly increase the reluctance of the flux circuit so that flux flows through rotatable ring 40 as indicated. The flux change in ring 40 causes a current to be induced in winding 47 in the rotatable ring, the induced current having an instantaneous direction as indicated (i.e., out of the paper).

Figure 6:
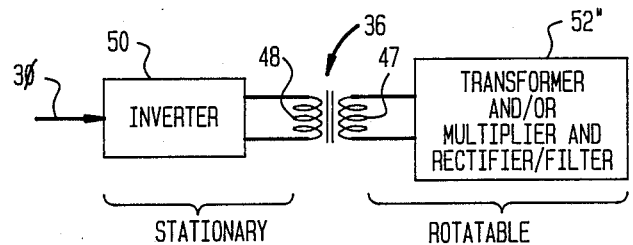
FIG. 6 shows a further electrical schematic for use with the present invention.

FIG. 6 indicates the manner in which a high-frequency alternating current can be applied to the windings in the stationary member. Specifically, FIG. 6 shows stationary innverter 50 to which a three-phase power line is connected for driving transformer and/or multiplier and rectifier/filter 52 mounted on the rotatable member by means of inductive coupling means 36 which may take the form shown in FIG. 5a.

An alternate arrangement of the inductive coupling means shown in FIG. 5a is shown in FIG. 5b wherein rotatable ring 40A is provided with radially displaced grooves 44A, 44B in face 41A; and stationary ring 42A is provided with complementary radially displaced grooves 45A, 45B in face 43A. Each of the grooves in the two rings contains azimuthally wound conductors 46A defining separate windings 47A, 47B in the rotatable ring, and 48A, 48B in the stationary ring. The instantaneous direction of current in each winding is as shown in FIG. 5b. In the windings contained in stationary ring 42A, currents having instantaneous polarities as shown may be applied by a power supply. Such currents induce currents of complementary polarities in the windings contained in rotatable ring 40A.

Figure 7:
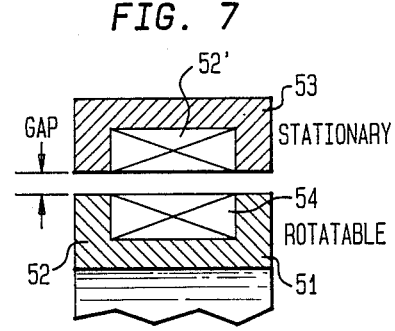
FIG. 7 is a further embodiment of the present invention.

A still further embodiment of the inductive coupling means of the present invention is shown in FIG. 7. In this embodiment, cylindrical face 50 of rotatable ring is 51 radially displaced from but closely adjacent to opposite cylindrical face 50 of stationary ring 53. The axes of cylindrical faces 50, 52 are coincident with axis 18 of the scanner. Each face contains at least one groove containing winding 54 in the form of an azimuthally wound conductor. While FIG. 7 shows rings each containing a single groove, it is clear that each ring could also contain two grooves as shown in FIG. 5b.

Figure 4:
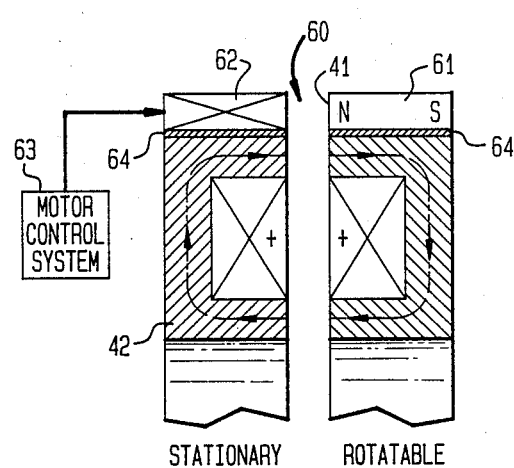
FIG. 4 is a more detailed view of stationary and moveable rings modified for the purpose of driving the rotatable ring relative to the stationary ring.

In a conventional CT scanner, rotation of the rotatable member relative to the stationary member is achieved by various expedients including direct mechanical coupling between the stationary and rotatable members. According to the present invention, means 60 (FIG. 4) are provided for rotating rotatable member 40 relative to stationary member 42. As shown in FIG. 4, means 60 comprises a plurality of permanent magnet segments 61 mounted azimuthally on the outer periphery of rotatable ring 40. The polarity of adjacent segments is reversed. That is to say, if the north pole of a given magnetic segment is adjacent end face 41 of ring 40, the segments on either side of the given segment are arranged such that their south poles are adjacent face 41.

Means 60 also includes a plurality of individually operable electromagnetic segments 62 mounted on the outer periphery of stationary ring 42. Each of these electromagnets can be energized by motor control system 63 such that rotation of ring 40 relative to ring 42 can be effected by alternating the polarity of excitation of electromagnet segments 62. Similarly, reversed polarity energization of the electromagnet segments can be used for braking rotation of the rotatable ring. As shown in FIG. 4, both segments 61 and 62 are separated from the respective rings by layer 64 of Mu-metal having a high magnetic permeability and low hysteresis loss.

Figure 2:
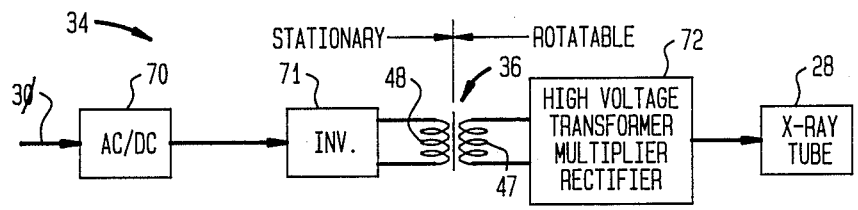
FIG. 2 is an electrical schematic showing the manner in which power is transferred inductively in the apparatus shown in FIG. 1.

FIG. 2 shows, schematically, the manner in which power may be supplied to X-ray tube 28 from stationary power supply 34 of the scanner. Specifically, three phase power is applied to AC/DC converter 70 the output of which is applied to inverter 71 whose output drives winding 48 of the stationary ring in the configuration of FIG. 4. Due to the magnetic coupling between windings 47 and 48 in the stationary and rotatable rings, power is transferred to AC/DC converter 72 located on rotatable member 16. The output of converter 72 is applied to X-ray tube 28 for the purpose of causing the latter to produce X-rays. The configuration of inductive coupling means 36 shown in FIG. 2 would involve a groove configuration such as shown in FIG. 5a or in FIG. 7.

Figure 3:
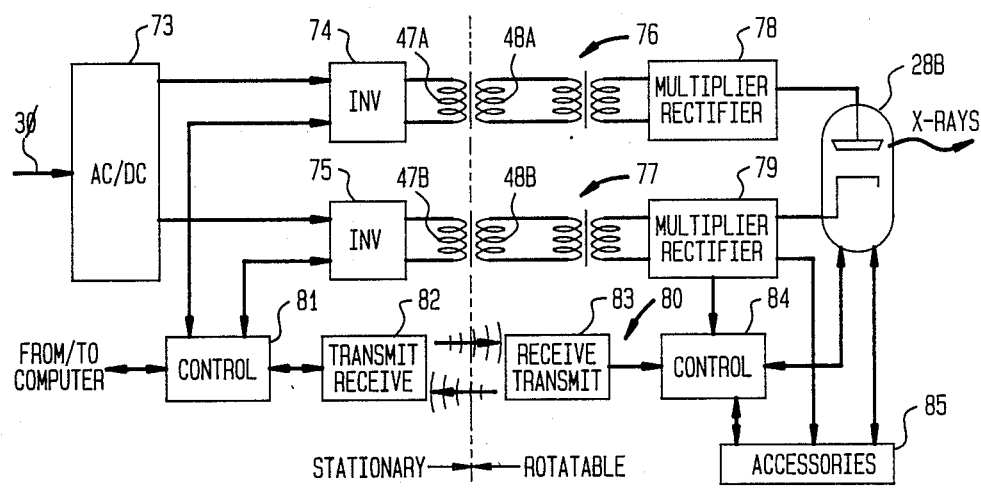
FIG. 3 is a modification of the electrical schematic circuit as shown in FIG. 2.

FIG. 3 shows a schematic arrangement suitable for the inductive coupling means shown in FIG. 5b. That is to say, three phase power is applied to AC/DC converter 73 which divides the input into two outputs supplied to inverters 74, 75. Each of these inverters establishes a power transmission channel 76, 77 which supplies current to the two windings associated with stationary ring 42 shown in FIG. 5b. The currents induced in the windings in rotatable ring 40 are applied to AC/DC converters 78, 79 for the purpose of producing, across the anode to cathode electrodes of X-ray tube 28B, a sufficient voltage for effecting the generation of X-rays. The arrangement shown in FIG. 3 is advantageous because it provides a natural way to divide the power supplied to the tube into two components, one that feeds the anode of the tube and one that feeds the cathode. Thus, the anode can be supplied with power at +75 KV and the cathode can be supplied with power at −75 KV.

To provide controls for the operation of X-ray tube 28 and other accessories 85, an auxiliary channel indicated by reference numeral 80 is usually provided in a CT scanner. That is to say, control information generated at 81 for the operation of tube 28 is applied to transmitter/receiver 82 located on the stationary member. A typical transmitter/receiver is one which produces a laser or an IR beam which is received on the rotatable member by a complementary transmitter/receiver 83. Information for controlling the X-ray tube and accessories is modulated onto the laser or IR beam by controller 81; and upon demodulation, controller 84 is effective to control the operation of the X-ray tube and accessories.

A conventional CT scanner is also provided with various accessories designated generally by reference numeral 85 on the rotatable member. Power for these accessories may be tapped from converter 79. Alternatively, a separate inductively coupled channel can be provided for powering the accessories.

The invention is also applicable to the "rotate-rotate" design where the detectors are mounted on the rotating member. In that case, the "accessories" 85 include the detectors and their associated circuitry. The data measured by the detectors are transmitted back to the stationary member via the same or separate high bandwidth transmit/receive channel, preferably digital.

The advantages and improved results furnished by the method and apparatus of the present invention are apparent from the foregoing description of the preferred embodiment of the invention. Various changes and modifications may be made without departing from the spirit and scope of the invention as described in the claims that follow.

I claim:
1. A CT scanner comprising:
(a) a static gantry member having a central axial aperture defining a central axis;
(b) a rotatable member mounted on said gantry member for rotation about said central axis;
(c) patient support means located inside said aperture on said central axis;
(d) an input power source associated with said gantry member;
(e) inductive coupling means responsive to said input power source for transmitting electrical power from said gantry member to said rotatable member;
(f) power conversion means mounted on said rotatable member for converting the electrical power into direct current at a high voltage suitable for X-ray production; and
(g) an x-ray tube mounted on said rotatable member and operable in response to power transferred to said rotatable member for producing x-ray beams passing through said central axis;
(h) said inductive coupling means including a highly permeable ring mounted on said gantry member, a highly permeable ring mounted on said rotatable member, at least one winding on the ring mounted on said gantry member, and at least one winding on the ring mounted on said rotatable member, each of the windings having an axis coincident with said central axis and being in the form of an azimuthally wound conductor; and
(i) wherein the rings have opposed annular faces each of which contains at least one annular groove, and said conductive means includes a circumferential conductive winding located in each annular groove, and power supply means for applying an alternating electrical current to one of said windings whereby an alternating electrical current is induced in the other winding, wherein said opposed annular faces define planes perpendicular to said central axis.

2. An apparatus according to claim 1 including means for rotating said rotatable member, said last named means including a plurality of permanent magnet segments of alternating polarity mounted azimuthally on said rotatable member about an axis coincident with said central axis, and a plurality of electromagnet segments mounted azimuthally on said static member about an axis coincident with said central axis, said permanent magnet segments being operatively located relative to said electromagnet segments for effecting rotation or braking of said rotatable member relative to said static member upon selective application of electrical current to said electromagnet segments.

3. A CT scanner according to claim 1 wherein said permanent magnet segments are mounted on the ring mounted on the rotatable member, and the electromagnet segments are mounted on the ring mounted on said static member.

4. A CT scanner according to claim 1 wherein two annular grooves are provided in each annular face of the rings, and said inductive coupling means includes a circumferential conductive winding located in each annular groove, said power supply means being constructed and arranged so that a high frequency alternating electric current is applied to each winding in one of said rings for inducing alternating electrical current in the other winding of the other of said rings.

5. A CT scanner according to claim 4 wherein the direction of current flow in the one of the windings in said one ring is opposite to the direction of the current flow in the other of the windings in said one ring.

6. A CT scanner according to claim 1 wherein said one winding is on the stationary ring and wherein said apparatus includes a high voltage utilization device mounted on the rotatable member, and to which the alternating electrical current induced in said other windings is applied.

7. A CT scanner according to claim 1 wherein said annular faces define cylindrical surfaces concentric with said central axis.

8. A CT scanner comprising:
(a) a static gantry member having a central axial aperture defining a central axis;
(b) a rotatable member mounted on said gantry member for rotation about said central axis;

(c) patient support means located inside said aperture on said central axis;

(d) an inut power source associated with said gantry member;

(e) inductive coupling means responsive to said input power source for transmitting electrical power from said gantry member to said rotatable member;

(f) power conversion means mounted on said rotatable member for converting the electrical power into direct current at a high voltage suitable for x-ray production; and (g) an x-ray tube mounted on said rotatable member and operable in response to power transferred to said rotatable member for producing x-ray beams spasing through said central axis;

(i) said inductive coupling means including a highly permeable ring mounted on said gantry member, a highly permeable ring mounted on said rotatable member, at least one winding on the ring mounted on said gantry member, and at least one winding on the ring mounted on said rotatable member, each of the windings having an axis coincident with said central axis and being in the form of an azimuthally wound conductor; and (j) wherein the rings have opposed annular faces each of which contains at least one annular groove, the winding on each ring being in the groove therein, wherein said opposed annular faces define planes perpendicular to said central axis.

9. A CT scanner according to claim 8 wherein said annular faces define cylindrical surface concentric with said central axis.

10. A CT scanner according to claim 8 including power supply means for applying a high frequency alternating electric current to the winding on the ring mounted on the gantry member whereby an alternating electrical current is induced in the winding on the ring mounted on the rotatable member, and circuit means on said rotatable member responsive to the current induced in the winding on the ring mounted on the rotatable member for operating said x-ray tube.

11. A CT scanner according to claim 10 wherein said power supply means includes a stationary high frequency inverter section, and said scanner includes a high voltage section on the rotatable member for driving said x-ray tube, said inductive coupling means being constructed and arranged to transmit power from said inverter section to said high voltage section.

12. A CT scanner comprising:
(a) a static gantry member having a central axial aperture defining a central axis;
(b) a rotatable member mounted on said gantry member for rotation about said central axis;
(c) patient support means located inside said aperture on said central axis;
(d) an input power source associated with said gantry member;
(e) inductive coupling means responsive to said inut power soure for transmitting electrical power from said gantry member to said rotatable member;
(f) power conversion means mounted on said rotatable member for converting the electrical power into direct current at a high voltage suitable for x-ray production; and
(g) an x-ray tube mounted on said rotatable member and operable in response to power tranferred to said rotatable member fr producing x-ray beams passing through said central axis;

(h) said inductive coupling means including a highly permeable ring mounted on said gantry member, a highly permeable ring mounted on said rotatable member, at least one winding on the ring mounted on said gantry member, and at least one winding on the ring mounted on said rotatable member, each of the windings having an axis coincident with said central axis and being in the form of an azimuthally wound conductor;

(i) the rings have opposed annular faces each of which contains at least one annular groove, the winding on each ring being in the groove therein;

(j) power supply means for applying a high frequency alternating electric current to the winding on the ring mounted on the gantry member whereby an alternating electrical current is induced in the winding on the ring mounted on the rotatable member, and circuit means on said rotatable member responsive to the current induced in the winding on the ring mounted on the rotatable member for operating said x-ray tube; and (k) wherein each of the opposed faces of said rings contains a pair of annular grooves that are concentric about said central axis, there being a circumferential conductive winding located in each annular groove.

13. A CT scanner according to claim 12 including means for rotating said rotatable member, said last named means including a plurality of permanent magnet segments of alternating polarity mounted azimuthally on said rotatable member about an axis coincident with said central axis, and a plurality of electromagnet segments mounted azimuthally on said gantry member about an axis coincident with said central axis, said permanent magnet segments being operatively located relative to said electromagnet segments for effecting rotation or braking of said rotatable member relative to said gantry member upon the selective application of electrical current to said electromagnet segments.

14. A CT scanner according to claim 13 wherein said permanent magnet segments are mounted on the ring mounted on the rotatable member, and the electromagnet segments are mounted on the ring mounted on the gantry member.

15. A CT scanner according to claim 3 including electrical powered accessories on sair rotatable member, an auxiliary inductive coupling channel for transmitting electrical power from said gantry member to said rotatable member, and circuit means for applying power transmitted by said auxiliary channel to said accessories.

16. A CT scanner according to claim 15 wherein said inductively coupled means includes a DC to AC/DC power supply on said rotatable member, the input to said AC/DC poewr supply being tapped from the input to said high voltage section, and the output of said AC/DC power supply driving said accessories.

17. A CT scanner according to claim 15 wherein said auxiliary channel is separate from said inductive coupling means.

18. A CT scanner according to claim 17 wherein said auxiliary channel includes a high frequency power supply having an inverter stage mounted on said gantry member, and an output stage mounted on said rotatable member.

19. A CT scanner according to claim 12 wherein said power supply means is constructed and arranged to apply a high frequency alternating electrical current to each winding on the ring mounted on the gantry member for inducing alternating electrical current in each winding of the ring mounted on the rotatable member.

20. A CT scanner according to claim 19 wherein the direction of current flow in one of the windings on the ring mounted on said gantry member is opposite to the direction of the current flow in the other of the windings on the last mentioned ring.

21. A CT scanner according to claim 20 wherein said circuit means includes converter means responsive to said induced alternating electrical current for producing a high voltage drive for said x-ray tube.

22. A CT scanner according to claim 21 wherein said converter means includes a transformer and a rectifier.

23. A CT scanner according to claim 22 wherein said converter means includes a voltage multiplier.

* * * * *